United States Patent [19]

Plotkin et al.

[11] Patent Number: 5,243,089

[45] Date of Patent: Sep. 7, 1993

[54] ALK-1-ENYL ETHERS

[75] Inventors: Jeffrey S. Plotkin, Monsey, N.Y.; Kolazi S. Narayanan, Palisades Park; Paul D. Taylor, West Milford, both of N.J.

[73] Assignee: ISP Investments Inc., Wilmington, Del.

[21] Appl. No.: 867,561

[22] Filed: Apr. 13, 1992

Related U.S. Application Data

[63] Continuation-in-part of Ser. No. 417,135, Oct. 4, 1989, abandoned.

[51] Int. Cl.$^5$ .................. C07C 41/00; C07C 43/11
[52] U.S. Cl. .................... 568/673; 568/616
[58] Field of Search .................. 568/616, 673

[56] References Cited

U.S. PATENT DOCUMENTS 4,703,114 10/1987 Mori .................. 568/616
4,814,514 3/1989 Yokota .................. 568/616

FOREIGN PATENT DOCUMENTS 012310 1/1979 Japan.

OTHER PUBLICATIONS

Gigg, R. J. Chem. Soc., Perkin Trans. 1, (3) 712-18 1979.

Primary Examiner—Paul J. Killos
Attorney, Agent, or Firm—Marilyn J. Maue; Joshua J. Ward

[57] ABSTRACT

This invention relates to an alk-1-enyl ether having the formula

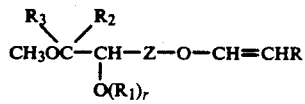

and to the process for its preparation.

10 Claims, No Drawings

ALK-1-ENYL ETHERS

This application is a continuation-in-part of Ser. No. 417,135, filed on Oct. 4, 1989, abandoned.

In one aspect this invention relates to novel alk-1-enyl ethers which can be cationically cured by heat and light radiation to form coatings and adhesives. In another aspect the invention relates to the reaction composition and the process for preparing said alk-1-enyl ethers.

BACKGROUND OF THE INVENTION

Polyallyl ethers derived from polyols and carbohydrates, particularly allylated pentaerythritol, trimethylpropane, and starches and sugars have been widely investigated as monomers suitable for protective coatings. These materials are attractive since they undergo autoxidative polymerization in contact with air. However, because of slow curing rates, color formation and relatively poor substrate bonding strength, films of these allyl ethers have limited commercial use (see ALLYL COMPOUNDS AND THEIR POLYMERS by C. E. Schildknecht, Wiley Interscience, 1973). Additionally many of these monomers and oligomers are thermally unstable and decompose to give off an objectionable odor characteristic of acrolein.

Attempts to prepare high molecular weight monoallyl ethers by free radical or ionic polymerizations have not been successful and result in low molecular weight product in admixture with substantial quantities of unreacted material which is difficult to separate. According t to British Patent 730,670, the polymerization of a allyl glycidyl ether benzene solution in the presence of 3% ditertiary butyl peroxide at 155° C. resulted in a product having a molecular weight of only 500 which was contaminated with a significant quantity of unconverted allyl glycidyl ether. Obviously such materials are unsuitable as protective coatings.

Although esters, which are electron accepting and require free radical initiation for UV curing, are not comparable to electron donating ethers which are highly reactive in cationically induced reactions, it is noted for the sake of full disclosure that certain ester blends of acrylated bisphenol A epoxy resins and ester blends of acrylated aromatic urethanes have been cured by UV exposure to provide rigid coatings. This work is reported by Byron K. Christmas et al. in 1988 (Specialty Chemicals 8(1) 24–6). However, these ester blends are not UV curable by cationically induced systems. Thus, as to be expected, their curing rates are comparatively slow, i.e. 7.5–100 ft/min with few exceptions up to 150 ft/min as compared to 300–500 ft/min achieved with cationically initiated UV radiation. Also, the coating properties of these blends display highly unpredictable results ranging from 0%–100% adhesion and MEK resistance from 1 to about 50 in most cases.

Accordingly, it is an object of the present invention to avoid the use of esters and to overcome the above deficiencies by the use of certain alkenyl derived ethers which are readily polymerizable in cationically initiated systems to provide thermally stable compounds having superior coating properties.

Another object is to provide films which consistently show good adhesion and high resistance to chemical attack.

Another object of this invention is to provide an economical and commercially feasible process for rapid curing of coated materials.

Still another object is to provide metal and glass coatings and finishes which are not subject to coloration over extended periods of use.

These and many other objects of the invention will become apparent from the following description and disclosure.

THE INVENTION

In accordance with this invention there is provided a novel, cationically induced, radiation curable, -enyl ether monomer, oligomer or polymer which can be prepared by the reaction of an alk-i-enyloxy oxirane with methanol. The reaction is illustrated by the following equation:

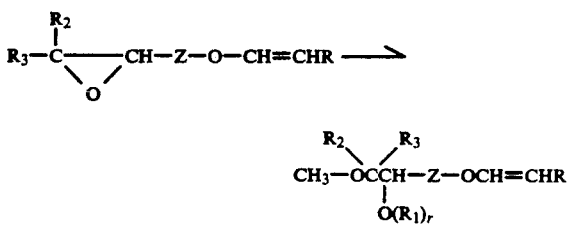

wherein $R_2$ and $R_3$ are each independently hydrogen, $C_1$ to $C_6$ alkyl, alkenyl, haloalkyl or haloalkenyl;

Z is an optionally alkoxylated $C_1$ to $C_8$ aliphatic hydrocarbon;

R is hydrogen or $C_1$ to $C_6$ alkyl;

r has a value of rom 1 to 300;

$R_1$ is hydrogen when r is one and when r has a positive value,

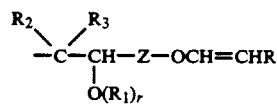

Thus, increasing amounts of epoxide component per hydroxide group in the reaction mixture are reflected in a corresponding progression of ring opened oxide groups substituted in the molecule of the final product.

Accordingly, when the condensation reaction employs prop-1-enyloxy methyl oxirane with methanol in a molar ration of 6:1, the product of the reaction is

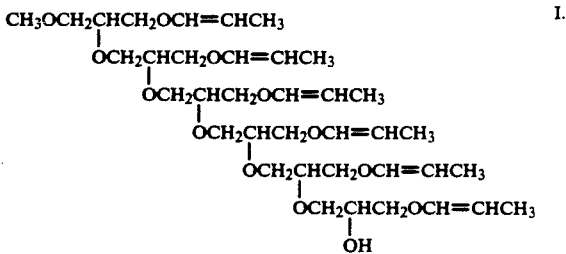

When the same condensation reaction is carried out using a 2:1 molar ratio of the oxirane to methanol, the corresponding product has the structure

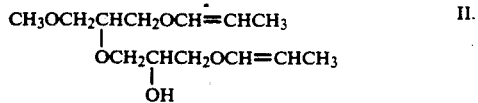

When a ratio of 1:1 oxirane to methanol is employed the product is

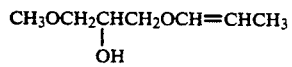 III.

The alk-1-enyloxy oxirane reactant contains from 5 to 28 carbon atoms, examples of which include 1-methyl-2-(prop-1-enyloxy) oxirane, (3-ethenyloxy propyl) oxirane, (4-ethenyloxy-butyloxy) methyl oxirane, 1-butyl-2-[2-(but-1-enyloxy) ethyl] oxirane, [4-(prop-1-enyloxy) butyl] oxirane, [2-(prop-1-enyloxy) ethyl] oxirane, 1-butyl-2[(but-1-enyloxy) ethyl] oxirane, [(prop-1-enyloxy) methyl] oxirane, [2-(vinyloxy) ethyl] oxirane, i-ethyl-2-[(prop-i-enyloxy)methyl] oxirane, 1-methyl-1-ethyl-2-[3-(hex-1-enyloxy)propyl] oxirane, 1-methyl-2-[2-(but-1-enyloxy) ethyl] oxirane, 1-ethyl-2-[4-(vinyloxy)butyl] oxirane, (ethenyloxy methyl) oxirane, ;-propyl-2-[2-(prop-1-enyloxy) ethyl] oxirane, 1,1-dimethyl-2-[2-(but-1-enyloxy) ethyl] oxirane, 1-hexyl-2-[8-(prop-1-enyloxy) octyl] oxirane, etc.

The mole ratio of methanol to oxirane reactant can vary between about 1:1 and about 1:300, preferably from about 1:1 tn about 1:50, depending upon the degree of —H substitution desired in the product.

The reaction is carried out in the presence of a base catalyst such as, e.g. sodium or potassium metal, sodium or potassium methoxylate, hydroxide, alkoxide, hydride, phenoxide, or an alkaline earth metal hydroxide or alkoxide. Also, alkali or alkaline earth metal salts of reactant A can be employed. The catalyst is employed in a concentration of between about 0.1 and about 5 wt. %, preferably between about 0.4 and about 1 wt. %, based on total reactants.

An inert solvent such as toluene, xylene, benzene; ethers such as alkyl ethers, e.g. methyl ethyl ether, diethyl ether, dibutyl ether, 1,2-dimethoxyethane, bis(2-methoxyethyl) ether, tetrahydrofuran; ketones such as methyl ethyl ketone; amides such as N-methyl-pyrrolidone, dimethyl formamide, N-ethyl-pyrrolidone; esters such as butyrolactone and ethyl acetate; nitriles such as acetonitrile and benzonitrile, cyclic carbonates such as ethylene and propylene carbonates and the like can be added to the reaction mixture if desired.

The present reaction is effected in the liquid phase by agitating the reactants under a blanket of inert gas, e.g. nitrogen, argon, etc., at a temperature within the range of between about 50° and about 150° C. under from about atmospheric pressure up to about 1,000 psi when volatile reactants are employed in the reaction mixture. The reaction takes place over a period of from about 1 to 8 hours. Preferred reaction conditions include a temperature of between about 90° and about 135° C. under a pressure not exceeding 200 psi for a period of from about 2 to 4 hours.

The products of this process are useful as molding resins, adhesives and as highly solvent resistant coating materials which undergo substantially instantaneous curing thermally or curing by irradiation to provide clear, colorless, flexible films when applied to a substrate.

Having thus generally described the invention, reference is now had to the accompanying examples which illustrate preferred embodiments but which are not to be construed as limiting to the scope of the invention as more broadly set forth above and in the accompanying examples.

EXAMPLE I Into a glass reactor equipped with a mechanical stirrer, nitrogen inlet, condenser, and thermometer was introduced 100 g. of methanol, 145 g. of (prop-1-enyloxymethyl)oxirane and 0.25 g. of sodium methoxide was combined. This mixture was stirred at 50° C. for 2 hours under a blanket of nitrogen. The reaction was cooled, the excess methanol removed by rotary evaporation and the product recovered in greater than 90% yield by simple flash distillation. The proton NMR spectrum identified the product as having the formula:

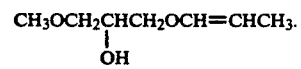

EXAMPLE II

The above reaction is repeated except that 290 g. of [(eth-1-enyloxy)methyl] oxirane is substituted for [(prop-1-enyloxy)methyl] oxirane. The product is

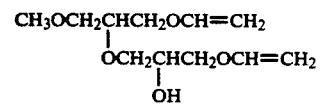

It will be understood that many modifications and substitutions can be made in the above examples to provide the novel compounds of this invention. For example, other oxiranes, such as [(but-1-enyloxy)butyl] oxirane, [(pent-1-enyloxy)butenyl] oxirane, [(prop-1-enyloxy)methyl] dimethyl oxirane, butenyloxy ethyl epoxide and the like can be substituted in the foregoing examples.

What is claimed is:

1. The alk-1-enyl ether having the formula

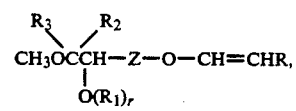

wherein $R_2$ and $R_3$ are each independently hydrogen $C_1$ to $C_6$ alkyl, alkenyl, halo alkyl or halo alkenyl;

Z is an optionally alkoxylated $C_1$ to $C_8$ aliphatic hydrocarbon;

R is hydrogen or $C_1$ to $C_4$ alkyl;

r has a value of from 1 to 300;

$R_1$ is hydrogen when r is one and, when r has a positive value, $R_1$

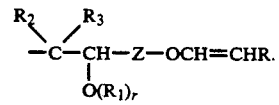

2. The alk-1-enyl ether of claim 1 wherein $R_2$ and $R_3$ are hydrogen.

3. The alk-1-enyl ether of claim 1 wherein Z is alkylene.

4. The alk-1-enyl ether of claim 3 wherein Z contains from 1 to 3 carbon atoms.

5. The alk-1-enyl ether of claim 1 wherein R is hydrogen or methyl.

6. The alk-1-enyl ether of claim 1 wherein $R_1$ is hydrogen.
7. The alk-1-enyl ether of claim 1 wherein $R_1$ is
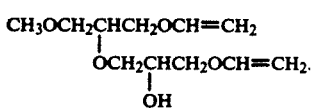
8. The alk-1-enyl ether of claim 3 having the formula
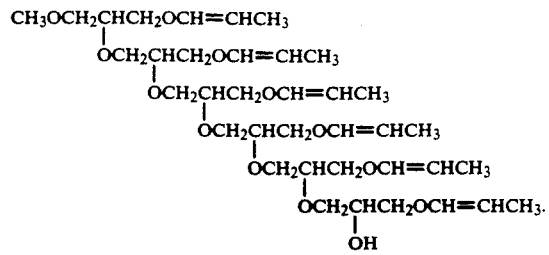
9. The alk-1-enyl ether of claim 3 having the formula
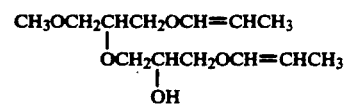
10. The alk-1-enyl ether of claim 3 having the formula
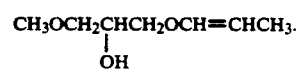
* * * * *